United States Patent
Griffin et al.

(10) Patent No.: US 10,190,950 B2
(45) Date of Patent: Jan. 29, 2019

(54) SEMI-AUTOMATED SAMPLING SYSTEM FOR ASEPTIC SAMPLING

(71) Applicant: General Electric Company, Schenectady, NY (US)

(72) Inventors: Weston Blaine Griffin, Niskayuna, NY (US); Chengkun Zhang, Rexford, NY (US); Kenneth Roger Conway, Clifton Park, NY (US); Reginald Donovan Smith, Schenectady, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 820 days.

(21) Appl. No.: 14/529,201

(22) Filed: Oct. 31, 2014

(65) Prior Publication Data

US 2016/0123848 A1  May 5, 2016

(51) Int. Cl.

| | |
|---|---|
| *G01N 1/14* | (2006.01) |
| *C12M 1/00* | (2006.01) |
| *C12M 1/32* | (2006.01) |
| *C12M 1/12* | (2006.01) |
| *C12M 1/34* | (2006.01) |

(52) U.S. Cl.
CPC .............. *G01N 1/14* (2013.01); *C12M 29/12* (2013.01); *C12M 33/06* (2013.01); *C12M 37/02* (2013.01); *C12M 41/00* (2013.01)

(58) Field of Classification Search
CPC ......... G01N 1/14; C12M 41/00; C12M 33/06; C12M 37/02
See application file for complete search history.

(56) References Cited

U.S. PATENT DOCUMENTS

| | | | |
|---|---|---|---|
| 4,198,862 A * | 4/1980 | Rubin | G01N 1/14 |
| | | | 73/863.83 |
| 4,999,307 A * | 3/1991 | Oakley | C12M 33/06 |
| | | | 435/309.1 |
| 6,817,256 B2 | 11/2004 | Mehra et al. | |
| 7,052,603 B2 | 5/2006 | Schick | |
| 7,186,378 B2 | 3/2007 | Dunfee | |
| 7,601,545 B2 | 10/2009 | Barringer | |

(Continued)

FOREIGN PATENT DOCUMENTS

CN  102661886 A  9/2012

*Primary Examiner* — Michael L Hobbs
(74) *Attorney, Agent, or Firm* — GE Global Patent Operation; Seema Katragadda

(57) ABSTRACT

A semi-automated sampling assembly configured for aseptic sampling at one or more instances from a sample source having a biological inoculum is provided. The semi-automated sampling assembly includes a sampling conduit, a recovery conduit, one or more sampling kits, and a pumping device. The sampling conduit includes a first port and a second port, where the first port of the sampling conduit is configured to be operatively coupled to the sample source. Further, the recovery conduit includes a first port and a second port, where the first port of the recovery conduit is configured to be operatively coupled to the sample source. Also, the second port of the recovery conduit is operatively coupled to at least a portion of the sampling conduit. Moreover, the one or more sampling kits are operatively coupled to the sampling conduit, and the pumping device is operatively coupled to the sampling conduit.

19 Claims, 7 Drawing Sheets

(56) References Cited

U.S. PATENT DOCUMENTS

| | | |
|---|---|---|
| 7,906,323 B2 | 3/2011 | Cannon et al. |
| 8,281,672 B2 | 10/2012 | Lee et al. |
| 8,337,755 B2 | 12/2012 | Bendele et al. |
| 8,394,635 B2 | 3/2013 | Key et al. |
| 8,640,556 B2 | 2/2014 | Hofman |
| 8,815,179 B2 | 8/2014 | Hofman et al. |
| 2008/0254533 A1* | 10/2008 | Antwiler ............ C12M 25/12 435/289.1 |
| 2011/0079095 A1 | 4/2011 | Bruecher |
| 2011/0201100 A1 | 8/2011 | Proulx et al. |
| 2013/0260390 A1 | 10/2013 | Goix et al. |
| 2016/0053296 A1 | 2/2016 | Zhang et al. |
| 2016/0122798 A1 | 5/2016 | Zhang et al. |

* cited by examiner

SEMI-AUTOMATED SAMPLING SYSTEM FOR ASEPTIC SAMPLING

BACKGROUND

Embodiments of the present specification relate to aseptic sampling, and more particularly to aseptic sampling at one or more instances in time.

Typically, in a cell culture process, growth media is used to nourish cells and carry away cell-secreted products. The growth media is provided continuously or intermittently to a culture vessel for in vitro culture of biological cells for: (1) recovery of cell-secreted proteins from the culture vessel, and/or (2) other purposes, such as expansion of cells. Further, the growth media is provided to the culture vessel via a flow path that is formed using suitable tubing. Often, this tubing is present as a closed system, where the closed system includes provisions for periodic or continuous replenishment of the growth media by introduction of fresh growth media.

It is often desirable to monitor the cell culture process. Further, monitoring of the growth media in the cell culture vessel and/or at one or more points in the flow path is an effective way of monitoring and/or controlling the cell culture process. Typically, monitoring of the cell culture process is performed by installing sensors in the culture vessel, as well as periodically drawing a portion of the growth media or a sample having a mix of cells and the culture media from the culture vessel for analysis. Thus, for example, analysis of the growth media before, during, and after passage through the culture vessel for monitoring one or more process conditions, such as nutrient components, cell-secreted proteins, cell-secreted metabolites, or the like may provide significant information regarding one or more of a number of viable cells in the culture vessel, a rate of nutrient consumption by the cells, a rate of product secretion, cell growth rates, stages of cell growth, presence or absence of subdivision of cells, and the like. Such information may be used to monitor the closed system and/or to indicate changes that may require alteration of the process conditions, the composition of the growth media, or the like to optimize the cell culture process.

Further, it is required for the cell culture process to be carried out under aseptic conditions as in the absence of the aseptic conditions the cells may be contaminated thereby resulting in contamination of products recovered therefrom and/or loss of cell viability. As a consequence, in vitro animal cell culture systems and their component parts are initiated and maintained under sterile conditions, with each portion or the entirety of the systems being sterilized prior to commencement of the process, and using sterile culture medium and uncontaminated seed cell stocks.

However, during sampling there is a need to ensure that sampling of the culture media or the sample is carried out in a manner to prevent introduction of contaminants into the pre-established sterile system. Conventional techniques for accomplishing this sterile withdrawal of the sample are elaborate, expensive, and time consuming. In addition, the conventional techniques for sterile withdrawal of the sample may compromise sterility of the culture vessel. By way of example, in some of the existing systems, the area from which the sample is to be drawn, be it the culture vessel or the flow path to or from the culture vessel, is provided with a sample port such as in the form of a short segment of tubing or other appropriate structures. The systems is then invaded via this sample port to withdraw a desirable quantity of the sample. Further, a portion of a biological inoculum, which is a mixture of the cells and the growth medium, is drawn from the culture vessel at different instances in time to monitor the cell culture process that is taking place in the culture vessel.

Each sampling instance requires drawing a portion of the sample from the culture vessel. Various tubes are attached to the ports or are passed through the ports of the culture vessel at different instances in time for different sampling instances. Any leakage or contamination in the tubing or in the connection between the culture vessel and the tubing may introduce contaminants in the culture vessel. Additionally, every sampling instance is accompanied by a user attaching some sort of tubing or device either directly or indirectly to the culture vessel, thereby increasing the risk of contamination of the inoculum. By way of example, a plastic sampling bag or a syringe may be attached to the tubing to collect the sample that is drawn from the culture vessel. In addition to the increased risk of introduction of the contaminants due to coupling of the sampling bags/syringes to the culture vessel, there is also a likelihood of a portion of the sample being left in the tubing after the sampling instance. This residual sample may then be inadvertently carried over to the next sampling instance, thereby jeopardizing the purity of the sample obtained in the next sampling instance. Further, each sampling instance increases the likelihood of contamination of the inoculum. Hence, it is desirable to ensure that sampling of the growth medium or culture fluid be carried out in a manner which avoids introduction of contaminants into the pre-established sterile system and provides a sample that is an accurate representative of the culture fluid.

In addition to the complex nature and risk of contamination associated with known sampling techniques, there also may exist an inherent limitation on the number or frequency of samplings which may be accommodated, either by reason of a limited number of sterilizable sequences to which a particular connector can be subjected to before severe degradation occurs or simply by reason of the inordinate amount of time needed to perform a sample withdrawal. These limitations may pose significant problems in situations where rapid and frequent sampling is required in order to monitor a potentially fast-changing situation. Still further, elaborate and/or time-consuming sampling techniques can add significantly to the overall cost of the culture process.

SUMMARY

In accordance with aspects of the present specification, a semi-automated sampling assembly configured for aseptic sampling at one or more instances from a sample source having a biological inoculum is provided. The semi-automated sampling assembly includes a sampling conduit, a recovery conduit, one or more sampling kits, and a pumping device. The sampling conduit includes a first port and a second port, where the first port of the sampling conduit is configured to be operatively coupled to the sample source. Further, the recovery conduit includes a first port and a second port, where the first port of the recovery conduit is configured to be operatively coupled to the sample source. Also, the second port of the recovery conduit is operatively coupled to at least a portion of the sampling conduit. Moreover, the one or more sampling kits are operatively coupled to the sampling conduit, and the pumping device is operatively coupled to the sampling conduit.

In another aspect of the present specification, a semi-automated sampling system for sampling a biological inoculum at one or more instances in time is provided. The semi-automated sampling system includes a sample source configured to house the biological inoculum and a semi-automated sampling assembly configured for aseptic sampling from the sample source. The semi-automated sampling assembly includes a sampling conduit, a recovery conduit, one or more sampling kits, and a pumping device. The sampling conduit includes a first port and a second port, where the first port of the sampling conduit is configured to be operatively coupled to the sample source. Further, the recovery conduit includes a first port and a second port, where the first port of the recovery conduit is configured to be operatively coupled to the sample source. Also, the second port of the recovery conduit is operatively coupled to at least a portion of the sampling conduit. Moreover, the one or more sampling kits are operatively coupled to the sampling conduit, and the pumping device is operatively coupled to the sampling conduit.

In yet another aspect of the present specification, a method for sampling a biological inoculum at one or more instances in time is provided. The method includes providing a sample source having an outlet port and a semi-automated sampling assembly from the sample source having the biological inoculum. The semi-automated sampling assembly includes a sampling conduit, a recovery conduit, one or more sampling kits, and a pumping device. The sampling conduit includes a first port and a second port, where the first port of the sampling conduit is configured to be operatively coupled to the sample source. Further, the recovery conduit includes a first port and a second port, where the first port of the recovery conduit is configured to be operatively coupled to the sample source. Moreover, the one or more sampling kits are operatively coupled to the sampling conduit, and the pumping device is operatively coupled to the sampling conduit. Further, the method includes mixing the biological inoculum in the sample source by circulating at least a portion of the biological inoculum using the pumping device, wherein at least a portion of the biological inoculum is pumped through at least a portion of the sampling conduit, recovery conduit, or both. Also, the method include drawing a sample into a sampling kit of the one or more sampling kits, and providing a first volume of a purging fluid in at least a portion of the sampling conduit using the pumping device.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
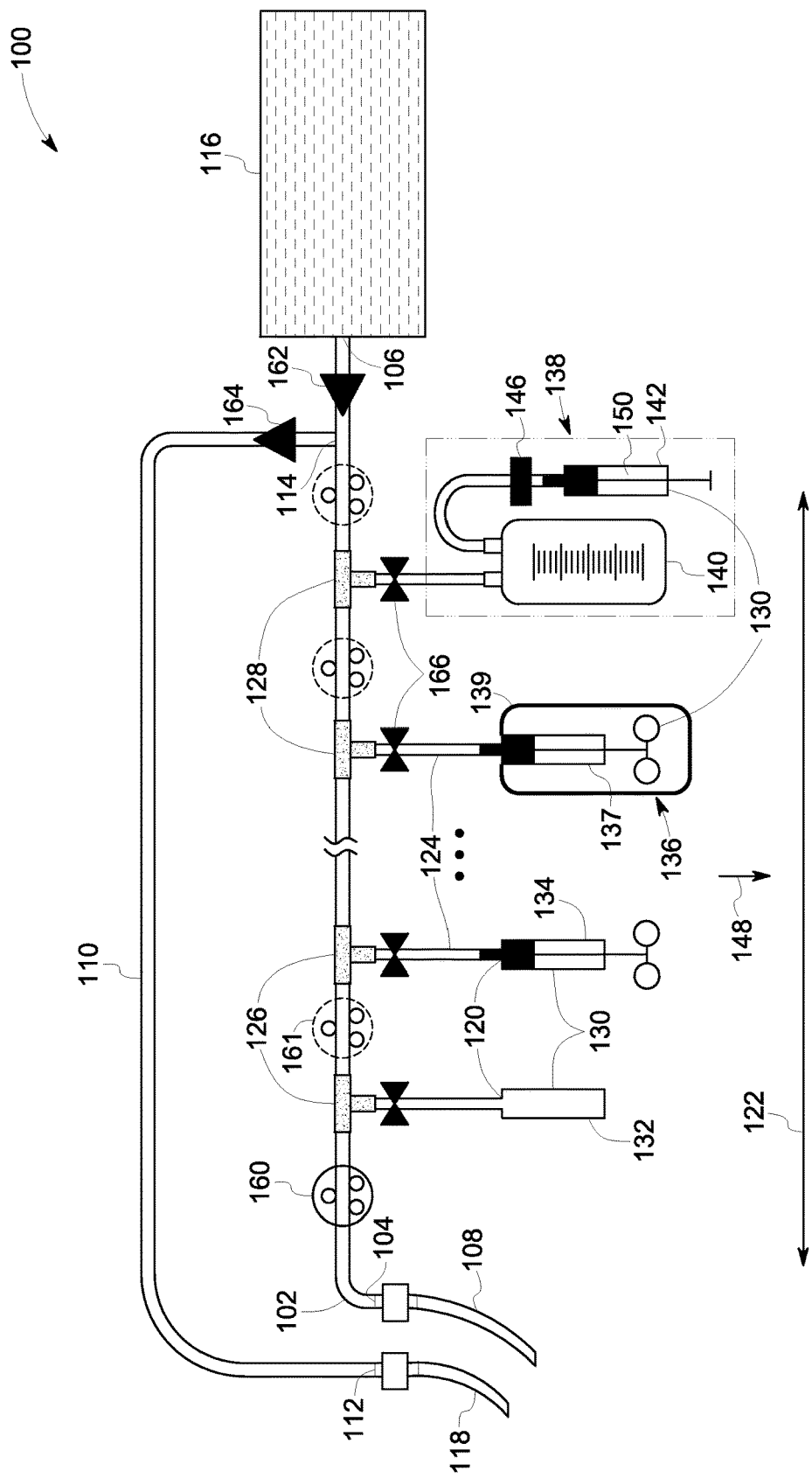
FIG. 1 is a schematic representation of an exemplary semi-automated sampling assembly configured to aseptically draw one or more samples from a sample source, in accordance with aspects of the present specification.

Embodiments of the present specification relate to semi-automated sampling assemblies, semi-automated sampling systems, and semi-automated sampling methods for aseptic sampling. Further, the semi-automated sampling assemblies, systems and methods are configured to aseptically draw one or more samples from a sample source at one or more instances in time. By way of example, for in vitro culturing of biological cells, the one or more samples may be drawn for intermittent sampling and monitoring of a cell culture for recovery of cell-secreted proteins or the partial or complete removal or testing of expansion of the biological cells. Advantageously, the semi-automated sampling assemblies, systems and methods of the present specification reduce or eliminate carryover of a residual sample from one sampling instance to another sampling instance. It may be noted that the residual sample may be a remnant of the sample that is left at least in a portion of a tubing of the semi-automated sampling assembly after completion of a sampling instance. In one embodiment, the semi-automated sampling assemblies, systems and methods are configured to provide provisions for purging at least a portion of the semi-automated sampling assembly after a sampling instance. The step of purging the portion of the sampling assembly after the sampling instance prevents carryover of the residual sample from a previous sampling instance to a subsequent sampling instance, thereby providing a sample that is an accurate representative of the culture fluid.

In certain embodiments, the semi-automated sampling assemblies are configured to aseptically draw a plurality of samples at different instances in time from the same sample source while obviating the need to attach a sampling kit to the sample source for each sampling instance. In particular, each sampling instance is not accompanied by labor intensive and time consuming step of aseptically attaching the sampling kit to the sample source. Moreover, in some embodiments, the sampling assemblies, systems and methods facilitate aseptic sampling by minimizing or preventing introduction of contamination (such as unintended microorganisms) in the sample source and/or the tubing of the semi-automated sampling assembly.

In certain embodiments, the semi-automated sampling assembly is configured to automate at least a purging step using a pumping device, such as, a motorized pump. Further, the pumping device may be configured to draw the sample and/or growth media into at least a portion of the tubing of the sampling assembly.

Furthermore, in some embodiments, the sampling assembly may be available as a standalone structure that is configured to be aseptically coupled to a sample source. In certain other embodiments, the sampling assembly may be available as a part of a pre-assembled sampling system, where the sampling system includes the sampling assembly aseptically coupled to a sample source. Further, the semi-automated sampling assembly is configured to be coupled to different types of sample sources. Moreover, the sample source may be configured to house and effect production of a protein, biological sample or other cultures of interest. The semi-automated sampling assembly may be pre-sterilized before coupling the sampling assembly to the sample source. In certain other embodiments, the sampling assembly may be sterilized after being coupled to the sample source. In some of these embodiments, the sampling assembly and the sample source may be sterilized collectively after being coupled to one another.

As will be appreciated, during cell culture of cells a growth medium is used to nourish the cells. It is well known that monitoring of an inoculum at one or more instances in time is useful in monitoring and controlling the cell culture process. To that end, an inoculum including a mixture of the cells and the growth medium is monitored by intermittently withdrawing a small portion of the inoculum for analysis. By way of example, analysis of the inoculum may be used to obtain information corresponding to number of viable cells in a culture vessel, rates of nutrient consumption by the cells and the rate of product secretion, cell growth rates, particular stages of cell growth or subdivision, and the like. Since the cell culture occurs over a period of time, sampling of the inoculum may be accomplished by drawing samples at instances separated in time. It may be noted that the monitoring may be performed to obtain information regarding the cell culture, and if required, to indicate a need for a change of one or more process conditions, growth medium composition, growth medium flow rate in the sample source, or the like, designed to optimize the cell culture process. The cell culture process is initiated and maintained under sterile conditions, with each portion or the entirety of the sampling system being sterilized prior to commencement of the process, and using sterile growth medium and uncontaminated seed cell stocks.

It may be noted that in case of conventional methods of sampling of the inoculum, there is a possibility of external impurities being introduced in the inoculum. Additionally, when sampling is performed at two or more instances in time, it is likely that a residue from a previous sampling instance is carried over to a next sampling instance. In the cell culture process it is highly desirable to: (1) prevent entry of external impurities in the sample source or associated components, and (2) minimize or prevent carryover of a residual sample from the previous sampling instance to the next sampling instance.

Before describing the present specification in further detail, various terms used in the present specification will be defined. Use of these terms does not limit the scope of the invention but only serve to facilitate the description of the embodiments.

As used herein, the singular forms "a," "an," and "the" include plural referents unless the context clearly dictates otherwise.

As used herein the phrase, "biological samples" refers to any particle(s), substance(s), extract(s), mixture(s), and/or assembly(ies) derived from or corresponding to one or more organisms, cells, and/or viruses. As will be appreciated, cells which may be cultured in an automated cell management system includes one or more cell types including, but not limited to, animal cells, insect cells, mammalian cells, human cells, transgenic cells, genetically engineered cells, transformed cells, cell lines, plant cells, anchorage-dependent cells, anchorage-independent cells, and other cells capable of being cultured in vitro. The biological sample also includes additional components to facilitate analysis, such as fluid (for example, water), buffer, culture nutrients, salt, other reagents, dyes, and the like. Accordingly, the biological sample may include one or more cells disposed in a growth medium and/or another suitable fluid medium.

As used herein, the term "sterile environment" refers to an environment that is substantially free of unintended microorganisms.

Moreover, as used herein, the term "sample source" refers to any suitable apparatus, such as a large fermentation chamber, bioreactor, bioreactor vessel and/or culture vessel, for growing organisms such as bacteria or yeast under controlled conditions for production of substances such as pharmaceuticals, antibodies, or vaccines, or for the bioconversion of organic waste. Further, the term "sample source" includes vessels for both aerobic and anaerobic cultivation of microbial, animal, insect and plant cells, and thus encompassing a fermentor.

Further, as used herein, "cell culture" entails growth, maintenance, differentiation, transfection, or propagation of cells, tissues, or their products.

Also, as used herein, the term "biological inoculum" refers to cell culture, cells suspended in growth media, suspension cells, cell aggregates, cells attached to beads and suspended in the growth media, and the like. Further, the term "biological inoculum" also refers to various cell types, such as, but not limited to, mammalian cell types (for example, Chinese Hamster Ovary (CHO), human embryonic kidney (HEK), human embryonic stem cells (hESC), T-cells, and the like), insect cell types, plant cell types, microbial cell types, and the like.

Moreover, as used herein, the phrase "growth medium" or "growth media" is used to refer to a liquid solution used to provide nutrients (for example, vitamins, amino acids, essential nutrients, salts, and the like) and properties (for example, similarity, buffering) to maintain living cells (or living cells in a tissue) and support their growth. Commercially available tissue growth medium is known to those skilled in the art. The phrase, "cell growth medium" as used herein means tissue growth medium that has been incubated with cultured cells in forming a cell culture; and more preferably refers to tissue growth medium that further includes substances secreted, excreted or released by cultured cells, or other compositional and/or physical changes that occur in the medium resulting from culturing the cells in the presence of the tissue growth medium.

Additionally, as used herein, the term "sampling instance" may be used to refer to an event of drawing a sample from a sample source at a given instance in time.

Further, as used herein, the term "aseptic sampling" refers to sampling while preventing entry of contamination or external impurities in the sample source or associated components.

Also, as used herein, the term "tubing" may refer to at least a portion of one or more of a sampling conduit, a recovery conduit, and one or more sub-conduits.

Moreover, it may be noted that the terms "sampling assembly" and "semi-automated sampling assembly" may be used interchangeably.

FIG. 1 illustrates a semi-automated sampling assembly 100 configured for aseptic sampling of one or more samples from a sample source (not shown in FIG. 1). In certain embodiments, the sample source may be a suitable culture vessel that is configured for cell culture, such as, but not limited to, cell expansion and growth. Further, the sample source may be configured to house a biological inoculum. In some embodiments, aseptic sampling may be performed to monitor the cell culture process occurring in the sample source. A sampling performed at a given time may be referred to as a sampling instance. In one embodiment, a plurality of sampling instances may be performed using the sampling assembly 100 in a time efficient and aseptic fashion.

In the illustrated embodiment, the sampling assembly 100 includes a sampling conduit 102 having a first port 104 and a second port 106. In the illustrated embodiment, the first port 104 of the sampling conduit 102 is configured to be operatively coupled to the sample source. Further, the second port 106 of the sampling conduit 102 is coupled to a purging fluid source, generally represented by reference numeral 116. The purging fluid source 116 is configured to provide a purging fluid to at least a portion of the sampling assembly 100. By way of example, the purging fluid source 116 may be configured to provide the purging fluid to the sampling conduit 102 to purge at least a portion of the sampling conduit 102.

In addition to the sampling conduit 102, the sampling assembly 100 also includes a recovery conduit 110. The recovery conduit 110 includes a first port 112 and a second port 114. The first port 112 of the recovery conduit 110 may be configured to be coupled to the sample source. Further, the second port 114 of the recovery conduit 110 may be coupled to the sampling conduit 102, or a purging fluid source 116, or both. As illustrated, the first ports 104 and 112 of the sampling and recovery conduits 102 and 110 may have additional components 108 and 118 to facilitate coupling of the first ports 104 and 112 to the sample source. In certain embodiments, the sampling conduit 102 may be configured to facilitate sampling of the biological inoculum disposed in the sample source. Further, the recovery conduit 110 may be configured to recover at least a portion of a residual sample that may be left in a tubing of the sampling assembly 100 after a sampling instance. After a sampling instance, the sampling assembly 100 is configured to recover the residual sample from the tubing of the sampling assembly 100 and return the recovered sample to the sample source, thereby aiding in purging the sampling assembly 100.

Further, the purging fluid source 116 is configured to provide the purging fluid for purging at least a portion of the sampling conduit 102 and/or the recovery conduit 110. Non-limiting examples of the purging fluid source 116 may include a growth media source, an osmotically balanced solution source, a sterile water source, an air source, an air filter, or combinations thereof. In a non-limiting example, the osmotically balanced solution may include a buffer solution, such as phosphate buffered saline. In one embodiment, the purging fluid source 116 may be configured to selectively provide the growth media to the sampling conduit 102, the recovery conduit 110, or both. In some embodiments, the purging fluid source 116 may be configured to provide the purging fluid before, during or after one or more sampling instances of a plurality of sampling instances. In some embodiments where the purging fluid source 116 is the growth media source, the purging fluid source may be pre-filled with the growth media before coupling the purging fluid source 116 to the sampling conduit 102, recovery conduit 110, or both. Further, in some embodiments, where the purging fluid source 116 is the growth media source, the purging fluid source 116 filled with growth media may be the only media coupled to a sampling system having the sampling assembly 100. Consequently, in these embodiments, components accompanying a growth media source, such as a pump, associated tubing, flow controllers, and flow regulators may be reduced accordingly due to use of a single growth media source. Accordingly, such sampling system and the sampling assembly 100 may entail use of a reduced overall number of components, and hence, complexity, while still providing a semi-automated functionally closed sampling system.

Additionally, the sampling assembly 100 includes a plurality of sub-ports 120 disposed along a first dimension (for example, a length) 122 of the sampling conduit 102. In particular, the sub-ports 120 may be disposed at respective ends of a plurality of the sub-conduits 124. Further, the plurality of sub-conduits 124 emanate from spaced-apart areas along the first dimension 122 of the sampling conduit 102. It may be noted that any suitable number of sub-conduits 124 may be pre-arranged along the first dimension 122 of the sampling conduit 102 depending upon the envisioned or desirable number of sampling instances in the plurality of sampling instances that may need to be performed during the cell culture process. Moreover, the sub-conduits 124 may be coupled to the sampling conduit 102 at corresponding connection junctions, generally represented by reference numeral 126. The sub-conduits 124 may be in fluidic connection with the sampling conduit 102. Further, the sub-conduits 124 may be coupled to the sampling conduit 102 using connectors 128. In one embodiment, the connectors 128 may be hollow T-shaped connectors, Y-shaped connectors, or any other suitably shaped connectors. In one embodiment, the sampling conduit 102 may be a continuous conduit. Alternatively, in another embodiment, the sampling conduit 102 may be a combination of interconnected portions of conduits. By way of example, the sampling conduit 102 may be formed from lengths of interconnected portions of the conduit or tubing that is connected at the connection junctions 126. In one such example embodiment, the sampling assembly 100 may be formed by one or more manifolds that are operatively coupled in fluidic communication with one another. In one embodiment, the manifolds may be made from hollow T-connectors, Y-connectors, or the like.

In certain embodiments, the sampling conduit 102 and the plurality of sub-conduits 124 may be made of poly-vinyl chloride (PVC), polyethylene (PE), ethylene-vinyl acetate (EVA), or combinations thereof. However, other polymeric materials may also be employed to form the sub-conduits 124. Liquid-tight and aseptic sealing at the connection junctions 126 may be facilitated by arranging suitable connectors 128 and the conduit 102 and sub-conduits 124. Further, the material of the conduit 102, sub-conduits 124, and connectors 128 may be suitable for sterilization processes. In one embodiment, the sampling assembly 100 may be pre-sterilized using sterilization methods, such as, but not limited to, gamma radiation sterilization, ethylene oxide (ETO) sterilization, hydrogen peroxide sterilization, or any other suitable sterilization methods.

In some embodiments, the sampling assembly 100 may include a plurality of sampling kits generally represented by reference numeral 130. Further, it may be noted that some or all of the sampling kits 130 may be same or different. The sampling kits 130 are aseptically coupled to the sampling conduit 102. In particular, each sampling kit 130 is coupled to a respective sub-port 120. Further, the sampling kits 130 are operatively coupled to their respective sub-ports 120 using the respective sub-conduits 124. It may be noted that a shape, a size and number of the sampling kits 130 employed in the sampling assembly 100 may vary based on sampling requirements. By way of example, the number of sampling kits 130 may be decided based on sampling instances and sample volumes that may be envisioned. Further, it may be noted that the sampling kits 130 may be sterilized before coupling the sampling kits 130 to the sub-ports 120. Alternatively, the sampling kits 130 may be sterilized after being coupled to the sub-ports 120.

In one embodiment, the sampling kits 130 may be made of plastic materials with the open sampling end suitably sized and shaped so as to be compatible within open exit ends of the sub-ports 120 of the sub-conduits 124. Further, a liquid-tight and aseptic seal may be achieved between the sampling kits 130 and the sub-conduits 124 through a force-fit. Additionally, the force-fit may be further enhanced by applying a compressive force about a periphery of the sampling conduit 102. Alternatively, a liquid-tight and aseptic seal may be achieved between the sampling kits 130 and the sub-conduits 124 using chemical bonding or mechanical fitting, such as one or more barbs.

Non-limiting examples of the sampling kits 130 may include a sampling pillow 132, a sampling syringe 134, an enclosed sampling syringe 136, an arrangement 138 where a syringe 142 is coupled to a sampling container 140, or combinations thereof. It may be noted that the sampling pillow 132 may be a resilient structure that after being pressed and released, is configured to regain at least a portion of its original shape. In the arrangement 138, the sampling container 140 in turn is coupled to the respective sub-port 120. In one embodiment, the sampling container 140 is a rigid plastic vessel or bottle that does not collapse substantially when the corresponding syringe 142 is pulled out to draw the sample into the sampling container 140.

Further, a filter 146 may be disposed between the syringe 142 and the sampling container 140. Moreover, the filter 146 may be an air filter that is configured to prevent any impurities from the surrounding environment from entering the sub-conduit 124 or the sampling conduit 102 and finally, the sample source. In a non-limiting example, the filter 146 may be a 0.22 micron membrane filter. In one embodiment, when the syringe 142 is drawn or pulled back in a direction represented by arrow 148, a barrel 150 of the syringe 142 is exposed to the air present in the surrounding non-sterile environment. More particularly, in operation, as a head of the syringe 142 is being pulled, a portion of the barrel 150 of the syringe 142 comes in contact with the air in the surrounding non-sterile environment. Advantageously, introducing the filter 146 between the syringe 142 and the sampling container 140 ensures that the sampling container 140 remains sterile and is not exposed to the air of the non-sterile environment or surfaces of the barrel 150 that may have been previously exposed to the non-sterile environment. In one example, it may be desirable to employ the sampling kit 138 in instances where it is required to draw a larger volume of the sample into the sampling container 140. Further, the enclosed sampling syringe 136 may include a syringe 137 enclosed in a suitable enclosure 139. In a non-limiting example, the enclosure 139 may be made of flexible plastic, such as nylon. Further, the syringe 137 may be enveloped in the enclosure 139 such that the enclosure 139 extends to a point of connection of the syringe 137 to the sampling conduit 102 so as to ensure maintenance of sterility through the enclosure 139 when the syringe 137 is operated to draw the sample.

Moreover, it may be noted that the arrangement of the sampling kits 130 disposed along the length 122 of the sampling conduit 102 may be in any convenient configuration. By way of example, the various sampling kits 130 may or may not be disposed in an equi-distance configuration along the sampling conduit 102. Further, relative positioning of the various sampling kits 130 may vary with respect to each other. Moreover, the sampling kits 130 may or may not extend in the same direction along the sampling conduit 102. By way of example, although not illustrated, in an alternative embodiment, the sampling kits 130 may be alternately disposed on opposite sides along the length 114 of the sampling conduit 102.

Further, in some embodiments, each sampling instance may use a corresponding sampling kit 130. Accordingly, the plurality of sampling kits 130 may be used to perform a plurality of sampling instances to aseptically draw a sample from the sample source. In a particular example, the number of sampling instances that may be carried out using the sampling assembly 100 may be less than or equal to the number of sampling kits 130 present in the sampling assembly 100. Further, since the sampling kits 130 are pre-attached to the sampling conduit 102, several steps that are associated with each sampling instance in conventional methods of sampling may be avoided. Non-limiting examples of such steps that need to be performed before or during a sampling instance for conventional sampling methods include: (1) disposing the sample source and any associated tubing in a sterile environment (for example, a laminar hood), (2) disinfecting at least a portion of a given sampling kit, (3) processing the tubing or the sample source to prepare the tubing, and/or the sample source to receive the sampling kit, where the processing may include disinfection, and (4) aseptically coupling the sampling kit to the sample source. The sampling assembly 100 of the present specification and associated sampling methods of the present specification circumvent the labor intensive and time consuming steps. In particular, the sampling assembly 100 and associated methods obviate the need for steps (1) to (4) that are otherwise required to be performed for each and every sampling instance in case of conventional sampling methods. Hence, in addition to aseptically sampling, the sampling assembly 100 of the present specification also provides time efficient sampling for a plurality of sampling instances.

Also, in some embodiments, the first ports 104 and 112 of the sampling and recovery conduits 102 and 110 may be initially closed for construction and sterilization of the sampling assembly 100. However, the first ports 104 and 112 may be adapted to be opened to form a sterile connection and fluidic communication with the sample source. Further, in operation, the biological inoculum present in the sample source may flow out of the sample source and into the sampling conduit 102 for a sampling instance. Alternatively, in another embodiment, the first ports 104 and 112 may be functionally closed ends of the sampling and recovery conduits 102 and 110. In this embodiment, the sampling assembly 100 may be coupled to the sample source by simply disengaging a portion of the sampling conduit 102 near the first ports 104 and 112 of the sampling and recovery conduits 102 and 110 to couple the sampling assembly 100 to the sample source.

Further, in certain embodiments, the sampling assembly 100 may be pre-sterilized and sealed. By way of example, in instances where the sampling assembly 100 is a standalone kit available to be coupled to an external sample source, the sampling assembly 100 may be pre-sterilized and sealed at the first ports 104 and 112 of the sampling and recovery conduits 102 and 110, respectively. In one embodiment, the first ports 104 and 112 may be temporarily sealed using sealing plugs (not shown in FIG. 1). At the time of use, the sterilized sampling assembly 100 may be coupled to the sample source by removing the sealing plugs and forming a sterile connection between the sampling assembly 100 and the sample source.

Additionally, the sampling assembly 100 includes a pumping device 160. The pumping device 160 may be configured to assist in purging at least a portion of the tubing of the sampling assembly 100. In certain embodiments, purging the portion of the sampling assembly 100 may include removing at least in part a residual sample from the tubing, where the residual sample may be disposed in the tubing as a result of a sampling instance. In some embodiments, the pumping device 160 in conjunction with the purging fluid source 116 may be configured to purge the portions of one or more of the sampling conduit 102, the recovery conduit 110, and one or more sub-conduits 124 by providing the purging fluid to the sampling conduit 102, the recovery conduit 110, and one or more sub-conduits 124 to remove the residual sample from the tubing of the sampling assembly 100. As will be described in greater detail with respect to FIGS. 3-7, in certain embodiments, the pumping device 160 may be configured to flow the purging fluid in one or more directions through at least a portion of the tubing of the sampling assembly 100. Accordingly, the sampling assembly 100 of the present specification is configured to facilitate maintenance of sterility of the sampling assembly and the inoculum disposed in the sample source. Further, the sampling assembly 100 is configured to prevent carryover of the residual sample from one sampling instance to one or more successive sampling instances. Non-limiting examples of the pumping device 160 may include a peristaltic pump and/or a syringe pump having a direction control valve. Although not illustrated, use of more than one pumping devices is also envisioned within the purview of the present application. By way of example, the sample source and the purging fluid source 116 may each be operatively coupled to their respective pumping devices. Reference numeral 161 represents some of the alternative or additional positions of pumping devices in the sampling assembly 100. Moreover, although in the illustrated embodiments of the present application, the pumping device is generally represented as being disposed between the sample source and the sampling kits 130, however, it may be noted that various other positions of the pumping device, for example, the pumping device 160, are envisioned. By way of example, the pumping device 160 may be disposed between any two sampling kits 130, or between the sampling kit 138 and an intersection of the second port 114 of the recovery conduit 110 and the sampling conduit 102.

Additionally, the pumping device 160 may also assist in withdrawing a sample from the sample source during a sampling instance. Although not illustrated, it is envisioned that in some embodiments, more than one pumping devices may be employed in the sampling assembly 100. By way of example, in instances where the second port 114 of the recovery conduit 110 is directly coupled to the purging fluid source 116, in addition to the pumping device 160 that is physically coupled to the sampling conduit 102, another pumping device may be coupled to the recovery conduit 110. Further, although not illustrated, in some embodiments, it is envisioned that the recovery conduit 110 and a flow regulator 164 may not be employed in the sampling assembly 100. In these embodiments, the pumping device 160 may be operated to draw a sample from the sample source into the sampling conduit 102 and up to a distal sampling kit, for example, the sampling kit 138 in the illustrated embodiment. However, in these embodiments, it needs to be ensured that the sample is not drawn further than the sampling kit 138. After drawing the sample, the pumping device 160 may be operated in a reverse direction to facilitate purging of the sampling conduit 102. Further, purging media may be drawn from the purging media source 116 to purge the sampling conduit 102.

Advantageously, in some embodiments, the pumping device 160 of the sampling assembly 100 may be programmed to perform sampling based on a desirable sampling pattern with minimal user intervention. In one example, the pumping device 160 may be programmed to perform sampling instances at periodic intervals. Moreover, since the series of steps that are desirable to obtain a sample can be similar for each sampling instance, the pumping device 160 may be pre-programmed to operate with minimal user intervention to carry out the sampling instances. By way of example, the pumping device 160 may be pre-programmed to pump desirable volumes of the sample or the purging fluid at one or more steps in a given sampling instance. In one embodiment, the pumping device 160 may be operatively coupled to a processor unit. In another example, a processor unit may be in-built into the purging device 160.

Additionally, the sampling assembly 100 may include one or more flow regulators that are configured to define and desirably limit the flow of the sample and/or the purging fluid in the tubing of the sampling assembly 100. For example, a flow regulator 162 may be operatively coupled to the purging fluid source 116 to ensure that the fluids in the tubing do not enter the purging fluid source 116. By way of example, the flow regulator 162 may be configured to restrict purging fluid or the sample flowing in the tubing of the sampling assembly 100 from entering into the purging fluid source 116, including the purging fluid and the sample. By way of example, during purging, the flow regulator 162 may be configured to ensure that the purging fluid that is once released by the purging fluid source 116 does not re-enter the purging fluid source 116. Further, the flow regulator 164 may be employed to facilitate a fluid flow in the recovery conduit 110 from the second port 114 of the recovery conduit 110 towards the sample source. Accordingly, the flow regulator 164 is configured to assist in recovery of the sample by facilitating the flow of the purging fluid from the sampling conduit 102 through the recovery conduit 110 towards the sample source.

In the illustrated embodiment, in addition to the flow regulators 162 and 164 both of which allow uni-directional flow of fluids in the sampling assembly 100, the sampling assembly 100 may also employ a plurality of flow controllers 166 to selectively allow and/or disallow the fluid flow in at least a portion of the tubing, for example, during sampling, purging, or when the sampling assembly is not in use. Further, each of the plurality of flow controllers 166 is coupled to a respective sub-conduit 124. Accordingly, a flow controller 166 corresponding to a respective sampling kit 130 may be opened to allow a sample to flow into the respective sampling kit 130 for a particular sampling instance, while maintaining the other flow controllers in a closed position. It may be noted that the open position of the flow controllers 166 allow the fluids to pass through the respective sub-conduits 124, whereas, the closed position of the flow controllers 166 does not allow the fluid to pass through the respective sub-conduits 124.

Further, it may be noted that various other alternative embodiments having fewer or greater number of flow regulators and/or flow controllers is envisioned. By way of example, in some embodiments, additional flow regulators may be deployed on the sub-conduits 124 and positioned between the sample kits 130 and the connector junctions 126, thereby allowing the sample to flow from the connector junctions 126 to the sampling kit 130. In another example, one or more flow controllers may be operatively coupled to the sample source and/or the purging fluid source 116.

Advantageously, the combination of the flow regulators 162 and 164 and flow controllers 166 is designed to facilitate sampling, purging at least a portion of the tubing including a portion of the sampling conduit 102, the recovery conduit 110, and/or corresponding sub-conduits 124, and preventing a residual sample from being left over in the tubing after a sampling instance. Further, the sampling assembly 100 is configured to enable aseptic sampling of the culture vessel one or more times during a process, such as, but not limited to, a cell expansion process, without substantial carry over contamination from one sampling instance to the next sampling instance.

In the illustrated embodiment, each sub-conduit 124 of the plurality of sub-conduits 124 may be used for a single sampling instance. Further, subsequent to the sampling instance, the respective sub-conduit 124 may be isolated using a corresponding flow controller. In some embodiments, a sealer, such as a mechanical sealer, a thermal sealer, or both may be used to seal the sub-conduit 124 at one or more locations. Non-limiting examples of the sealer may include a bar sealer. Further, in instances where the sub-conduit 124 is sealed at two or more locations, the sub-conduit 124 may be cut between the two or more sealed locations on the sub-conduit 124. By way of example, if the sub-conduit 124 is sealed at three locations, the sub-conduit 124 may be cut at a sealed location that is disposed between the other two of the three sealed locations. It may be noted that cutting the sub-conduit 124 between the other two sealed locations enables aseptically decoupling a corresponding sampling kit 130 from the sampling assembly 100. Further, cutting the sub-conduit 124 between two sealed locations ensures that the distal end of a remaining portion of the sub-conduit 124 that is still attached to the sampling conduit 102 remains hermetically sealed upon separation of the sampling kit 130.

In certain embodiments, samples may be drawn through a particular sub-conduit 124 using the flow controller 166. In operation, the sample may be drawn only in a portion of the sampling conduit 102, where the portion of the sampling conduit 102 extends between the sample source and a respective sub-conduit 124 that connects the sample source to the corresponding sampling kit 130. Further, in a non-limiting example, one or more samples may be drawn at same or different instances in time using the sampling kits 130 in a sequential order starting from the sampling kit 130 disposed closest to the sample source. However, using the sampling kits 130 in the sequential order may or may not be necessary.

Among other advantages of the sampling assembly 100 of the present specification, it is the ease with which the sampling assembly 100 may be constructed and easy availability of materials that are used in the sampling assembly, which may be easily and readily sterilized. In the illustrated embodiment of FIG. 1, for example, the sampling conduit 102, the recovery conduit 110 and the sub-conduits 124 lengths which make up the sampling conduit, as well as the sub-conduits 124 ending at sub-ports 120 may be made of any suitable biologically compatible material which is sufficiently rigid to maintain a liquid conduit bore therein and to permit interconnection using suitable connection devices, while at the same time being sufficiently flexible to permit bending and working as may be needed to effect connections. Further, the sampling assembly 100 is easy and convenient to use. By way of example, the sampling assembly 100 does not require a user to attach a sampling kit each and every time a sample needs to be withdrawn. Instead, the sampling kits are pre-attached in a hermetic manner to assist in easy and quick sampling for one or more number of times.

It may be noted that, although not illustrated, various other embodiments of the present specification are envisioned. By way of example, the sampling conduit 102 may be a T-shaped connector, where a secondary branch of the T-shaped connector may have one or more sub-ports. Also, instead of a single flow controller 162 for each sub-conduit 124 and sampling kit 130, two or more flow controllers may be operatively coupled to each sub-conduit 124, or the sampling kits 130. By way of example, additional flow controllers may be disposed between two sub-conduits 124 as a safety measure in the scenario where a corresponding flow controller 166 may fail to respond.

In certain embodiments, various components of the sampling assembly 100, such as, but not limited to, the sample source, the sampling conduit 102, the recovery conduit 110, the sampling kits 130, and the like are sterilized prior to being coupled to form the sampling assembly 100. Optionally, in some embodiments, the first ports 104 and 112 of the sampling and recovery conduits 102 and 110 which are to be arranged in liquid communication with the sample source may be closed upon initial construction. Further, the sampling assembly 100 may be sterilized by any suitable means, including irradiation.

Figure 2:
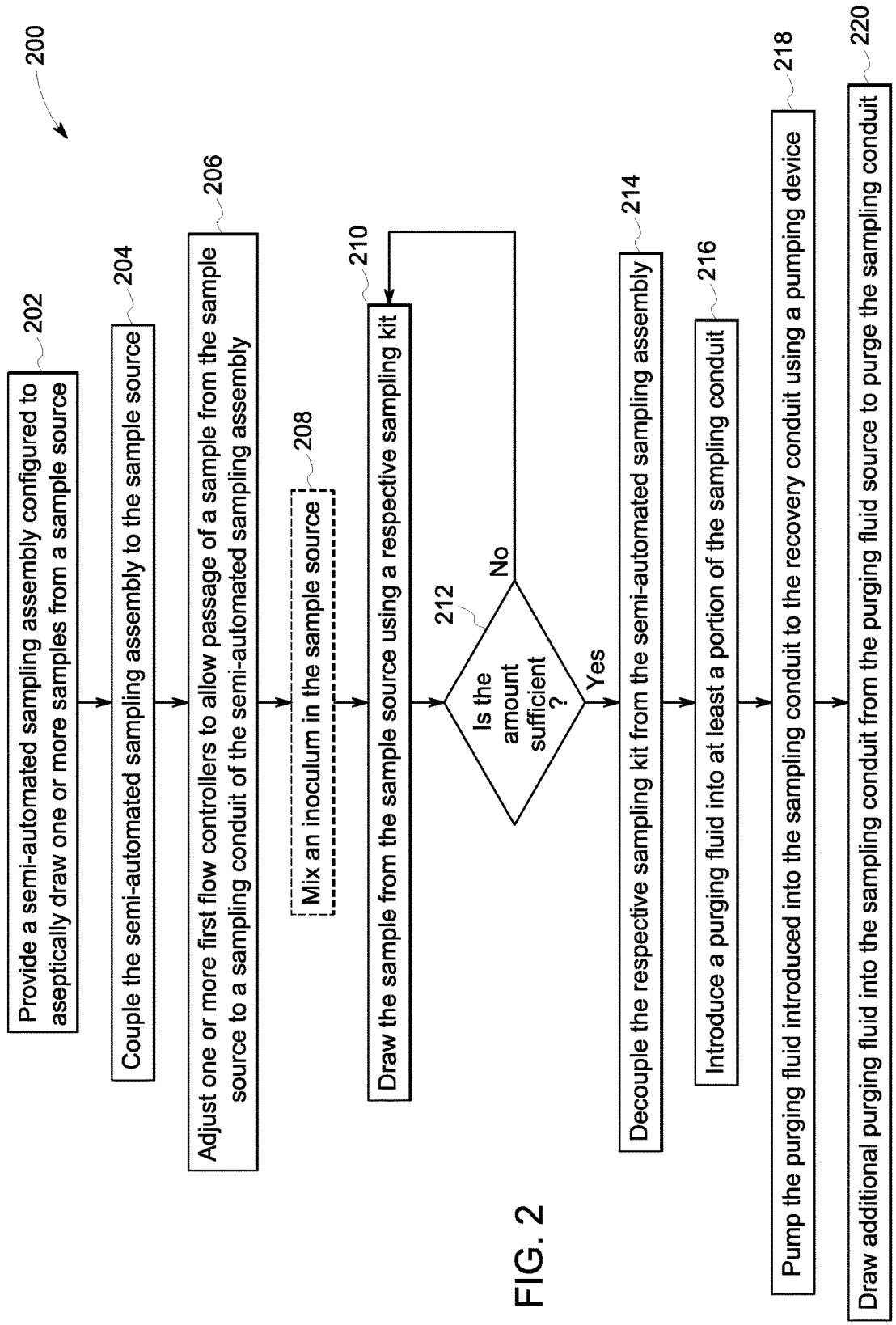
FIG. 2 is a flow chart of an exemplary method for aseptically sampling using a semi-automated sampling assembly, in accordance with aspects of the present specification.

FIG. 2 is an exemplary flow chart 200 of a method of using a semi-automated sampling assembly of the present specification to aseptically draw a sample from a sample source at one or more instances in time. In a non-limiting example, the samples may be drawn aseptically during a cell culture process. Advantageously, the method facilitates aseptically drawing the samples while preventing introduction of contaminants in the sampling assembly during or after a sampling instance. Further, the method enables time efficient and aseptic sampling at one or more instances in time. By way of example, since the sampling containers and/or sampling kits are pre-coupled to the sampling conduit in the sterilized pre-assembled sampling assembly, a user is not required to laboriously couple a sampling kit to the sample source for each sampling instance. It should be noted that in conventional methods where the user is required to couple the sampling kit to the sample source for each sampling instance, each sampling instance of coupling the sampling kit to the sample source is accompanied by increased likelihood of introduction of contaminants in the sample source. Accordingly, the probability of introduction of contaminants in the sample source increases drastically with the increase in the number of sampling instances. Further, in some embodiments, a pumping device of the sampling assembly may be programmed to perform sampling based on a desirable sampling pattern with minimal user intervention. In one example, the pumping device may be programmed to perform sampling instances at periodic intervals.

In certain embodiments, a sample mixture having a biological inoculum of cells to be cultured may be introduced into a sample source, such as, but not limited to, a culture unit, a bioreactor, or any other suitable vessel. Further, a growth medium may be introduced in the sample source, for example to nourish the cells in the sample source. Moreover, provisions (for example, flow controllers, flow regulators, or both) may be provided for the sampling conduit and/or the sampling kits such that the sampling kits and the sample source may not be undesirably influenced, for example, during the step of drawing the sample or following the step of drawing the sample. In one embodiment, the semi-automated sampling assembly may include the semi-automated sampling assembly of FIG. 1.

At step 202, a semi-automated sampling assembly configured to aseptically draw one or more samples from a sample source is provided. The semi-automated sampling assembly is a pre-assembled sterilized arrangement that includes a sampling conduit, a recovery conduit, a plurality of sub-conduits, a plurality of sampling kits, and one or more pumping devices. Additionally, each sub-conduit of the plurality of sub-conduits includes a corresponding sub-port. Further, both the sampling and recovery conduits include corresponding first and second ports. Moreover, the second port of the sampling conduit may be coupled to one or more pumping devices. Additionally, the second port of the recovery conduit may be coupled to the sampling conduit at a location on the sampling conduit disposed relatively closer to the second port of the sampling conduit. Further, one or more sub-ports of the sub-conduits are operatively coupled to a corresponding sampling kit of the plurality of sampling kits. The sampling kits may be sterilized before being coupled to their corresponding sub-ports.

Next, at step 204, the sampling assembly may be coupled to a sample source. In some embodiments, the respective first ports of the sampling and recovery conduits may be aseptically pre-coupled to the sample source. In one example, an arrangement having the sample source that is aseptically coupled to the sampling assembly may be provided at the beginning of the cell culture or cell expansion process. Alternatively, in some other embodiments, the sample source and the sampling assembly may be provided separately. In these embodiments, at the beginning of the first sampling instance of a plurality of sampling instances, the respective first ports of the sampling and recovery conduits may be coupled to the sample source. Once the respective first ports of the sampling and recovery conduits are coupled to the sample source, the sampling assembly may remain coupled to the sample source for at least the duration of the plurality of sampling instances, and even after the sampling is completed. Accordingly, the sampling assembly of the present specification eliminates the need for attaching individual sampling kits to the sample source at the beginning of each sampling instance. Consequently, the sampling assembly of the present specification provides a time efficient and an easy to use arrangement for performing aseptic sampling including the plurality of sampling instances. In one example, the respective first ports of the sampling and recovery conduits may be coupled to the sample source by thermal fusion to the tube pre-attached to the culture vessel, such as a bioreactor. It may be noted that in embodiments where the sampling assembly is pre-coupled to the sample source to form a sampling system, the sampling system may be available as a ready to use arrangement. In these embodiments, step 204 may be redundant.

At step 206, for a given sampling instance, one or more first flow controllers of the semi-automated sampling assembly may be adjusted to allow passage of a portion of the sample from the sample source to the sampling conduit. It may be noted that for the sampling kit adjacently disposed the sample source, if the corresponding flow controller is not disposed between the sample source and the corresponding sub-conduit it may not be required to adjust the corresponding flow controller. Optionally, if a plurality of second flow controllers is employed, one or more second flow controllers may be adjusted to allow the portion of the sample from the sample source to flow into a respective sampling kit.

Optionally, as represented at step 208, prior to step 210 of drawing the sample from the sample source, the biological inoculum disposed in the sample source may be mixed to increase homogeneity of the inoculum to ensure that the sample drawn in the given sampling instance is an appropriate representation of the cell population present in the sample source. In some embodiments, mixing of the inoculum may be performed by circulating the inoculum through a portion of the sampling conduit and the recovery conduit using the pumping device. In one example, a portion of the inoculum may be drawn into a portion of the sampling conduit and directed from the sampling conduit to the recovery conduit before being returned to the sample source. Once the portion of the inoculum is returned to the sample source, another portion of the inoculum may be drawn from the sampling conduit and circulated through the portion of the sampling conduit and returned to the sample source via the recovery conduit. This process of circulating a portion of the inoculum may be repeated a desirable number of times, as required. Further, the inoculum may be circulated in a continuous or intermittent fashion.

Next, at step 210, a portion of the sample may be drawn from the sample source in conjunction with use of the pumping device. In particular, the sample may be drawn from the sample source into the sampling conduit, or both the sampling and recovery conduits, and subsequently into the sampling kit using the pumping device that is coupled to a portion of the sampling conduit. Further, for the next sample instance, one or more first flow controllers may also need to be adjusted to allow the flow of the sample from the sample source to a respective sampling kit. Also, it may be noted that in some instances, orientation of the sample source may be adjusted to allow the sample to flow out of the sample source into the sampling conduit. In a non-limiting example where the sample is disposed in a portion of a volume of the sample source, the sample source may be tilted to allow the sample to flow to a port of the sample source that is in fluidic communication with the sampling conduit. In one embodiment, where the sampling kit is a sampling pillow, the sample may be drawn into the sampling pillow by first compressing the sampling pillow to remove at least a portion of the air disposed in the sampling pillow. Further, the air displaced from the sampling pillow travels through the corresponding sub-conduit and into the sampling conduit. Further, the pumping device may be used to move the air away from a portion of the sampling conduit disposed between the pumping device and the corresponding connector junction of the sampling pillow. Upon release of the air, a sample is drawn into the sampling pillow. In another embodiment, where the sampling kit is a sample pillow predisposed in a compressed configuration, with the release of a flow controller the sample pillow may self-inflate drawing in the sample disposed in the sampling conduit.

Further, a determination may be made whether the amount of the sample collected is equal to a desirable amount of the sample. Accordingly, at step 212, if it is determined that the amount of sample collected in the sampling kit is sufficient or more than the desirable amount, the operator may adjust the sampling kit. In embodiments where the sampling kit is a syringe, an operator may adjust a syringe plunger to obtain the desirable amount of the sample into the syringe. In some embodiments, a sub-conduit corresponding to a syringe in which the sample is to be drawn contains air initially and/or a portion of the sampling conduit disposed between the sample source and the syringe contains a fluid, such as the biological inoculum or the purging fluid. In these embodiments, prior to drawing the sample in a syringe, the syringe may be manipulated such that the syringe may first be filled with air from the corresponding sub-conduit and then may be filled with the sample from the sampling conduit drawn through the corresponding sub-conduit.

Moreover, at step 212, in instances where an amount of the sample drawn into the syringe is insufficient, the syringe may be manipulated to draw additional sample into the syringe. However, in instances where the amount of the sample drawn into the syringe is in excess of the desirable amount, the excess amount of the sample may be reintroduced into the corresponding sub-conduit. Further, the excess amount of the sample may be pushed back into the sub-conduit with the syringe being oriented such that any air in the syringe is not introduced into the sub-conduit. Once the desirable amount of the sample has been drawn into the syringe, the syringe may be oriented such that the air in the syringe is moved to an end of the syringe that is closest to the corresponding sub-conduit. The air in the syringe may then be pushed into the sub-conduit, thereby displacing the sample material contained within the sub-conduit into the sampling conduit. Filling the sub-conduit with air helps to limit sample carry over for subsequent sampling instances.

In some embodiments where the sampling kit is a sampling pillow, prior to sampling, the corresponding sub-conduit of the sampling pillow may contain air initially and the sampling conduit may contain fluid. To draw the sample into the sampling pillow, the sampling pillow may be at least partially compressed to displace the air within the sampling pillow. Upon release of the sampling pillow, the pillow may rebound to its original shape by first filling at least a portion of the sampling pillow with air present in the corresponding sub-conduit. Subsequently, the sampling pillow may continue to be filled with the sample from the sampling conduit via the corresponding sub-conduit. Moreover, in instances where the amount of sample drawn into the sampling pillow is more than a desirable amount, the excess amount of the sample may be reintroduced into the corresponding sub-conduit. In particular, the excess amount of the sample may be pushed back into the corresponding sub-conduit with the sampling pillow oriented such that any air in the sampling pillow is not displaced into the sub-conduit. Once the desirable amount of the sample is drawn into the sampling pillow, the sampling pillow may be oriented such that air in the sampling pillow floats to an end closest to the corresponding sub-conduit. The air in the sampling pillow may then be pushed into the corresponding sub-conduit displacing any sample material contained within the corresponding sub-conduit into the sampling conduit.

Also, in some embodiments, if it is determined that the quantity of the sample collected in the sampling kit is not adequate and is less than the desirable amount, some more sample may be drawn from the sample source (step 210) using a different sampling kit. And subsequent steps may be repeated accordingly.

At step 214, if the amount of the sample collected in the sampling kit is sufficient or more than sufficient, the corresponding sampling kit may be aseptically decoupled from the sampling assembly. In some embodiments, prior to decoupling, the sampling kit, one or more locations on the corresponding sub-conduit may be hermetically sealed. Further, the sampling kit may be decoupled from the sampling assembly by disengaging a portion of the sub-conduit from the sample assembly by cutting the sub-conduit between two sealed locations. Sealing the sub-conduit at one or more locations before disengaging helps in preventing introduction of any contaminants from the open end formed because of decoupling of the sampling kit.

Further, more sampling instances may be performed as and when desirable or until all the sub-ports, respective sub-conduits and respective sampling kits are utilized. In a particular embodiment, the sampling may be performed in a sequential order in the direction starting from the sample source and travelling towards the second port of the sampling conduit.

Subsequently, at step 216, purging fluid, such as, but not limited to, sterilized air and growth media, is introduced in at least a portion of the sampling conduit using the pumping device. Moreover, at step 218, the purging fluid introduced into the sampling conduit is pumped into the recovery conduit using the pumping device. Also, at step 220, additional purging fluid is drawn into the sampling conduit from the purging fluid source. In embodiments where a volume of the sampling conduit is less than or equal to a volume of the recovery conduit, a volume of the purging fluid introduced into the sampling conduit may displace the inoculum present in the sampling conduit by pushing the inoculum into the sample source. In certain embodiments, the purging fluid may be drawn from the purging fluid source due to the presence of the flow regulators that are operatively coupled to the sampling and recovery conduits. The volume of the purging fluid that is pumped through the sampling conduit to the sample source may be greater than a volume of the sampling conduit so as to further reduce the amount of residual sample in the sampling conduit.

Next, the pumping device may pump the purging fluid in the sampling conduit and through the recovery conduit before transferring the purging fluid to the sample source, thereby purging the recovery conduit of the biological inoculum. It may be noted that the flow regulator operatively coupled to the sampling conduit and/or the purging fluid source prevents the purging fluid from re-entering into the purging fluid source. The volume of the purging fluid pumped though the recovery conduit may be equal to the volume of the recovery conduit, but may be less than the volume of the sampling conduit. Further, as the recovery conduit is purged, a volume of the biological inoculum may be pulled into the sampling conduit from the sampling source. However, the pumping device may pump the purging fluid to the sample source from the purging fluid source via the sampling conduit, thereby purging the sampling conduit of the biological inoculum. It may be noted that a desirable amount of the purging fluid is drawn to ensure that only determined amount of the purging fluid is introduced in the sample source after each sampling instance.

Figure 3:
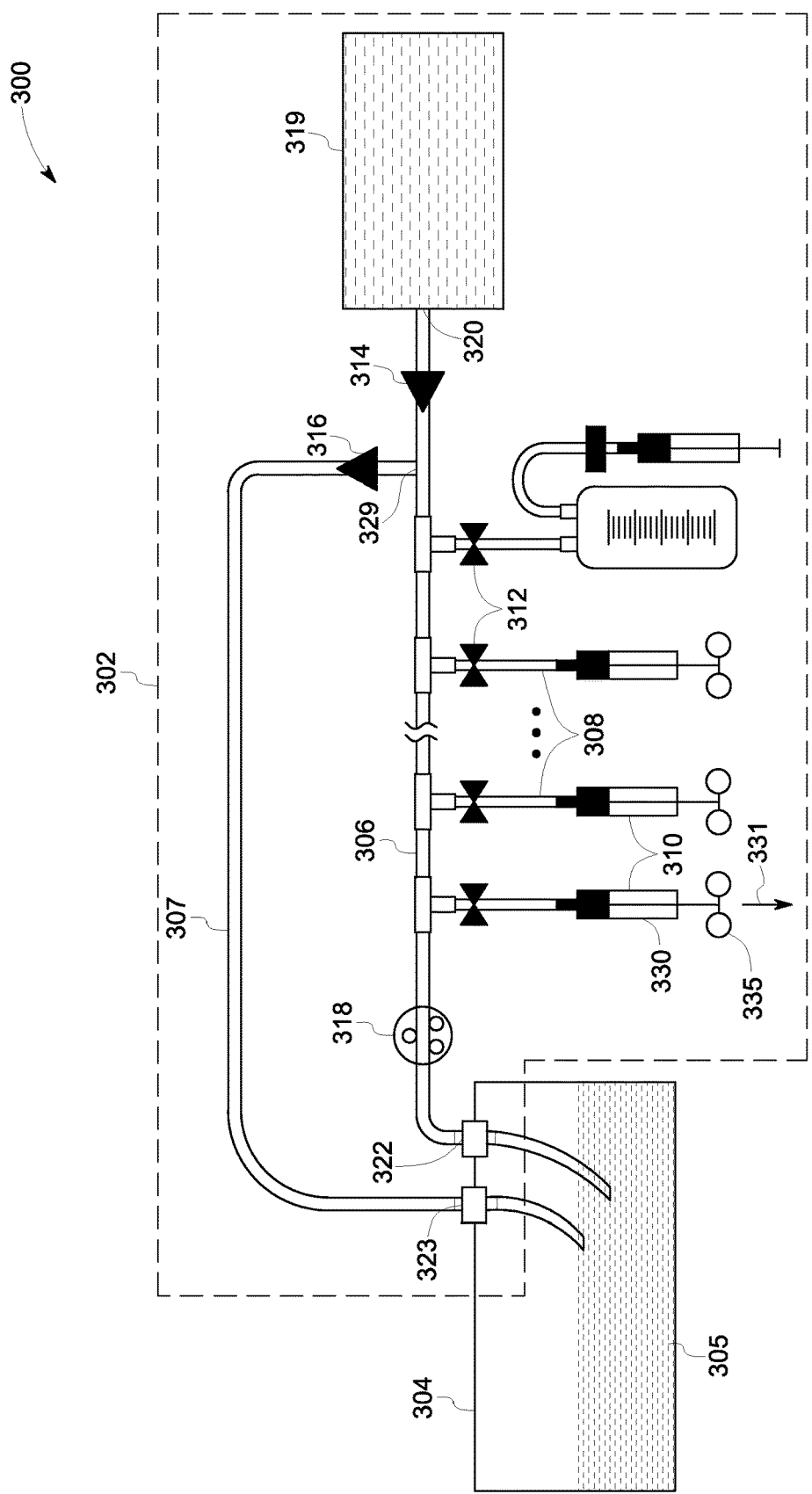
FIGS. 3-7 are schematic representations of steps involved in the method of aseptically sampling using the semi-automated sampling assembly of FIG. 1, in accordance with aspects of the present specification.

FIGS. 3-7 illustrate steps involved in a sampling instance using a semi-automated sampling assembly 300 of the present specification. By way of example, FIGS. 3-7 may be considered as schematic representations of steps involved in the method of using the semi-automated sampling assembly 300 to aseptically draw a sample from a sample source at one or more instances in time. FIG. 3 represents a schematic view of a sampling system 300 having a semi-automated sampling assembly 302 operatively coupled to a sample source 304 having a biological inoculum 305 for example, cell expansion. The sampling system 300 is configured to facilitate aseptically drawing one or more samples at one or more instances in time. In one example, the sample source 304 may be a culture vessel, such as a bioreactor, a fermentor, or any other suitable culture vessel. In the illustrated embodiment, the sampling assembly 302 includes a sampling conduit 306, a recovery conduit 307, a plurality of sub-conduits 308, and a plurality of sampling kits 310 coupled to the sampling conduit 306 via the sub-conduits 308. Further, the sampling conduit 306 includes a first port 322 and a second port 320. Also, the recovery conduit 307 includes a first port 323 and a second port 325. Further, the sampling assembly 302 also includes a plurality of flow controllers 312 and one or more flow regulators 314 and 316. Additionally, the semi-automated sampling assembly 302 includes a pumping device 318 and a purging fluid source 319.

Further, the pumping device 318 is coupled to a portion of the sampling conduit 306. The pumping device 318 may include a peristaltic pump, pinch-valve pump, or the like. Moreover, in instances where the sampling assembly 302 is available as a stand-alone ready to use arrangement, the first ports 322 and 323 of the sampling and recovery conduits 306 and 307 may be initially hermetically sealed. In a non-limiting example, removable seals (not shown in FIG. 3) may be used to hermetically seal the first ports 322 and 323 of the sampling and recovery conduits 306 and 307 to hermetically seal the sampling assembly 302. Further, the seals at the first ports 322 and 323 may be removed immediately at the time of coupling the first ports 322 and 323 to the sample source 304 to provide a fluidic communication between the sample source 304 and the sampling and recovery conduits 306 and 307. In the illustrated embodiment, the sampling assembly 302 is aseptically pre-attached to the sample source 304 using known techniques, such as tube fusion. In other instances, the sampling assembly 302 is pre-attached to the sample source 304 and is available as a single integrated unit that is ready to use. FIG. 3 illustrates one such exemplary integrated, ready to use sampling system. In particular, it may be noted that the sampling assembly 302 or the sampling system 300 is a pre-assembled and sterilized arrangement that is pre-fitted with the sampling kits 310, the purging fluid source 319 and the pumping device 318. Further, the pumping device 318 is configured to act as a pump to provide purging media, such as cell culture media, contained in the purging source 319 to the sample source 304. It may be noted that the pumping device 318 may be used to provide the purging media to the sample source 304 irrespective of the stage of the sampling. Further, if the purging fluid source 319 includes the cell culture media, the cell culture media of the purging fluid source 319 may act as the purging fluid.

Further, FIGS. 3-7 illustrate a sampling instance for drawing a sample into a selected sampling kit of the plurality of sampling kits 310. Moreover, in the illustrated embodiment, the selected sampling kit is a sampling syringe 330. The sample may be drawn into the sampling syringe 330 by pulling a head 335 of the sampling syringe 330 in a direction represented by reference numeral 331.

Figure 4:
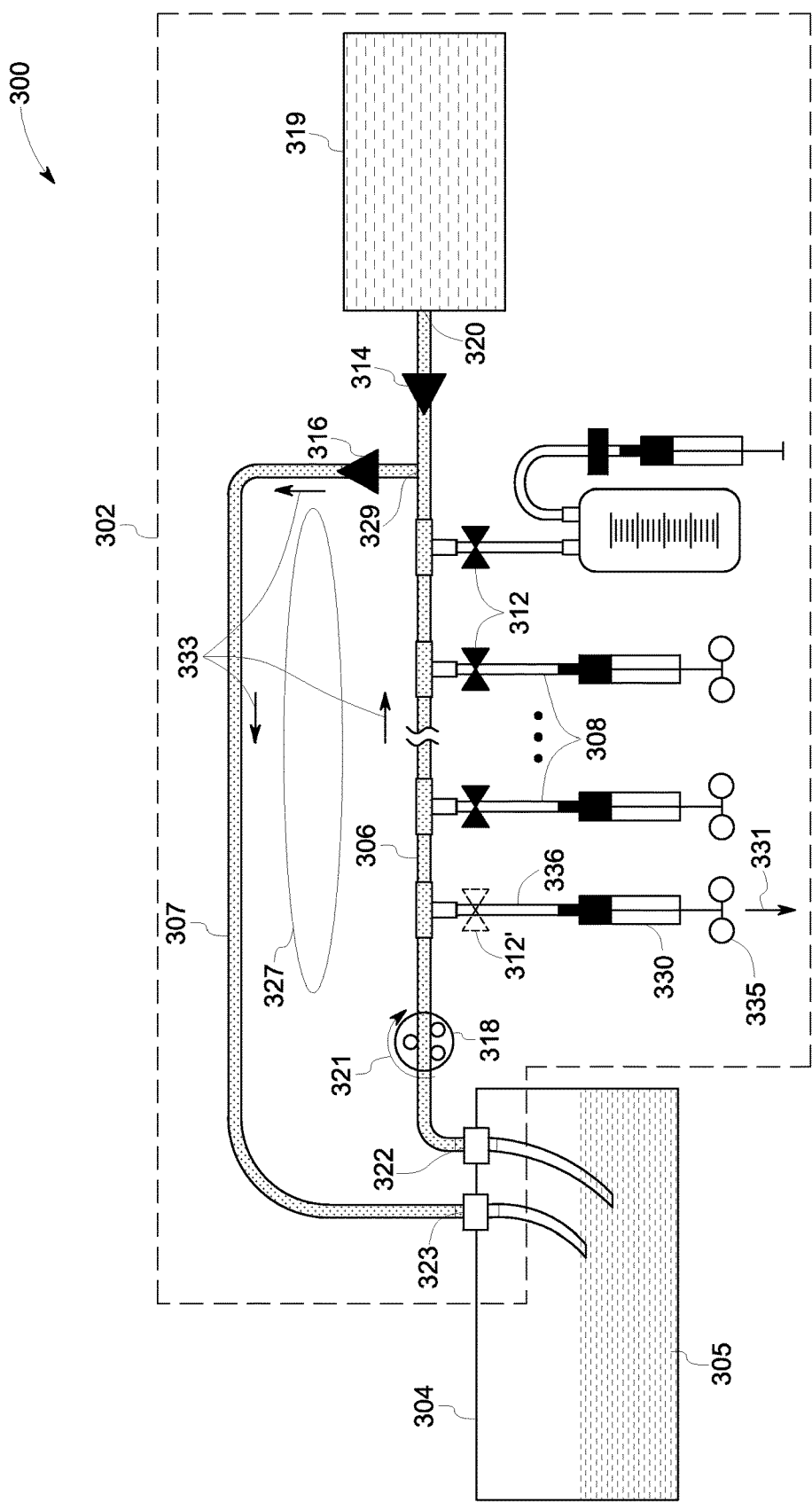

As illustrated in FIG. 4, the pumping device 318 is operated such that at least a portion of the biological inoculum 305 is drawn from the sample source 304 into at least a portion of the sampling conduit 306.

In certain embodiments, at least a portion of the biological inoculum 305 may be circulated in a loop, generally referenced by reference numeral 327, formed in the tubing of the sampling assembly 302. The loop 327 may be referred to as a sampling loop 327. The sampling loop 327 is formed primarily between the first port 322 of the sampling conduit 306 and may extend till the first port 323 of the recovery conduit 307 via a junction 329 formed at an intersection between the sampling and recovery conduits 306 and 307. Further, arrows 333 represent the direction of circulation of the biological inoculum 305 in the sampling loop 327. Circulating the biological inoculum 305 from the sample source through the sampling loop 327 enables mixing of the biological inoculum 305 in the sample source 304 prior to a sampling instance. Once the biological inoculum 305 is mixed well, the sampling may be performed by pulling the head 335 of the sampling syringe 330 in the direction 331. In one example, the pumping device 318 is a peristaltic pump and the direction of rotation of the pump is set to a clockwise direction, represented by reference numeral 321 to enable inoculum from the sample source to be drawn into the sampling conduit 306 via the first port 322 of the sampling conduit 306. In certain embodiments, a determined volume of the biological inoculum 305 may be pushed past a corresponding sub-conduit 336 of a given sampling kit 330 in which the sample needs to be collected for that particular sampling instance.

In some embodiments, the volume of the sample pushed past the sub-conduit 308 may be at least as large as a volume of the sample itself. Further, in these embodiments, after the sample is drawn into the sampling conduit 306 and before drawing the sample present in the sampling conduit 306 in the sampling kit 330, if the pumping device 318 is switched off, the sampling kit 330 may be used to pull the sample present between the sub-conduit 336 and the purging fluid source 319 into the sampling kit 330. Further, as the sample in the sampling conduit 306 is drawn into the sampling kit 330, an equivalent amount of the purging fluid from the purging fluid source 319 may be drawn into the sampling conduit 306 as a make-up volume. Accordingly, if the pump is switched off after drawing the sample into the sampling conduit 306, then an equivalent amount of the purging fluid needs to be present in the sampling conduit between the pumping device 318 and a junction 329. However, if the pump is maintained in a running condition during the sampling process, it may not be required to maintain the equivalent amount of the purging fluid in the sampling conduit 306.

It may be noted that while the first port 322 of the sampling conduit 306 is in physical contact with the inoculum, the first port 323 of the recovery conduit 307 may not be in physical contact with the inoculum 305. This way, the recovery conduit 307 may be mostly used to bring back fluids in the sample source 304 from the tubing of the sampling assembly 302. However, the recovery conduit 307 may not be configured to carry the inoculum 305 from the sample source 304 into the recovery conduit 307. Further, when initially filling the sampling loop 327 with the biological inoculum 305 from the sample source 304, the air present in the sampling loop 327 may be expelled directly into the purging fluid source 319, thereby preventing the air from entering the sample source 304 and damaging cells present in the biological inoculum. In the particular sampling instance using the sampling syringe 330, as represented by the dashed illustrations, the flow controller 312 may be adjusted to allow the sample to flow into the corresponding sub-conduit 336 of the plurality of sub-conduits 308.

In some embodiments, it may be desirable to perform the sampling while the biological inoculum 305 is being circulated. Further, it may be noted that the rotation rate of the pumping device 318 may be higher than a sample collection rate. If the rotation rate of the pumping device 318 is lower than the sample collection rate, the purging fluid may be drawn from the purging fluid source 319 into the sampling loop 327 due to the presence of flow regulators 314 and 316 that allow uni-directional flow in the sampling loop 327.

In other embodiments, sampling may occur when the pumping device 318 is stopped. However, when the sampling is performed after the pumping device 318 is switched off, it may be noted that an amount of purging fluid may be drawn into the sampling loop 327 when the sample is drawn into the sampling syringe 330. Accordingly, when the sampling is performed with the pumping device 318 being switched off, it may be desirable to ensure that there is a large enough sample volume downstream, for example, between the junction 329 and intersection of the sub-conduit 336 and the sampling conduit 306, such that the volume of the sample drawn into the sampling conduit 306 includes the biological inoculum 305 and not a combination of the biological inoculum 305 and the purging fluid pulled from the purging source 319.

Figure 5:
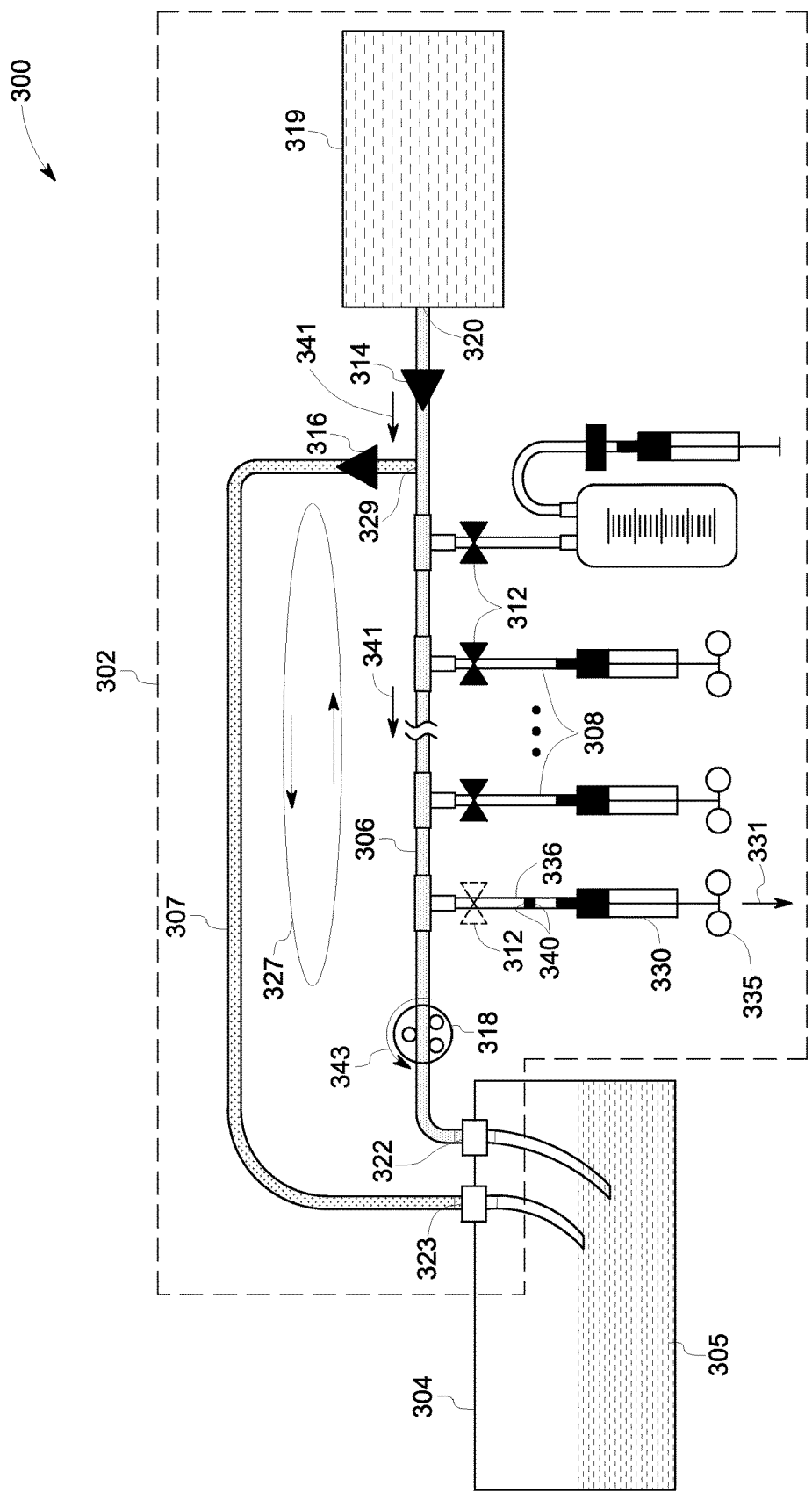

Next, as illustrated in FIG. 5, the corresponding sub-conduit 336 corresponding to the sampling syringe 330 is sealed at at least one location 340. In a non-limiting example, the sub-conduit 336 may be sealed at the three or more locations, generally represented by 340, using bar sealers. Further, the purging fluid may be drawn into a portion of the sampling conduit 306 using the pumping device 318. Arrows 341 represent the flow of the purging fluid in the sampling conduit 306. In instances where the pumping device 318 is a peristaltic pump, the direction of the pumping device 318 may be set to be in an anticlockwise direction, represented by reference numeral 343, to facilitate drawing the purging fluid from the purging fluid source 319 into the sampling conduit 306.

The amount of the purging fluid that is introduced in the sampling conduit 306 may be sufficient enough to purge the sampling conduit 306. In one embodiment, an amount of the purging fluid that is drawn from purging fluid source 319 into the sampling conduit 306 may be equivalent to a volume of the sampling conduit 306. It may be noted that the flow regulator 316 prevents any residual sample in the recovery conduit from entering into the sampling conduit 306. Further, the flow regulator 316 also allows the sampling loop 327 to serve as a connection for providing the purging fluid to the recovery conduit 307.

Figure 6:
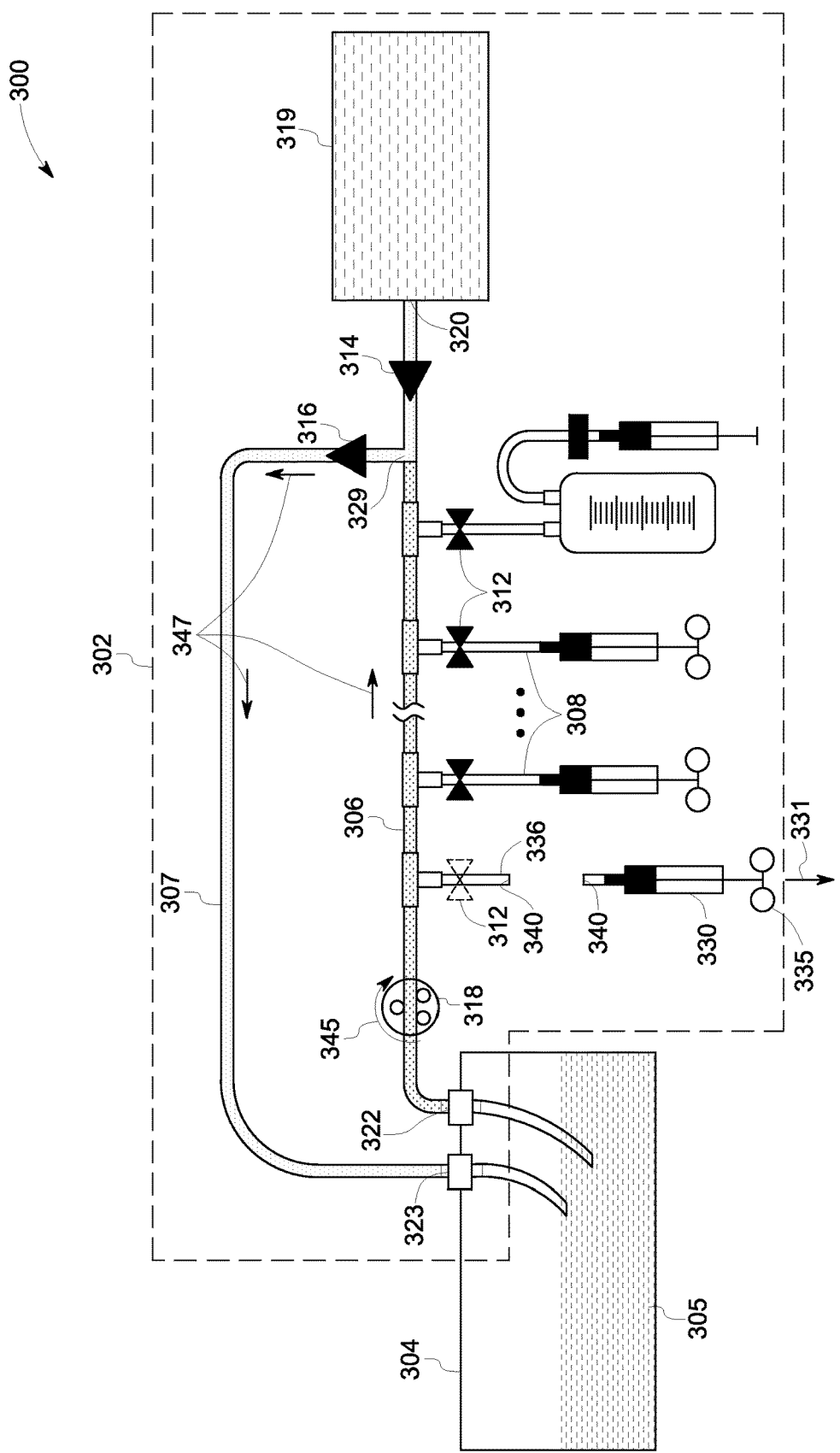

Further, as illustrated in FIG. 6, the purging fluid present in the sampling conduit 306 may be pumped through the sampling loop 327 to flush any residual sample from the sampling and recovery conduits 306 and 307 into the sample source 304. As illustrated by arrow 345, the direction of pumping may be reversed to flush the purging fluid from the sampling conduit 306 into the recovery conduit 307. It may be noted that the volume of purging fluid that is pumped in the previous step illustrated in FIG. 5 may be just enough to flush the residual sample out of the recovery conduit 307 and into the sample source. Also, it may be noted that a hold-up volume of the recovery conduit 307 may be less than a hold-up volume of the sampling conduit 306. In this way, only the purging fluid in the sampling conduit may be used to purge the residual sample from the recovery conduit 307.

Further, it may be noted that by providing the recovery conduit 307 with the purging fluid from the sampling conduit 306, the pumping device 318 may draw additional purging fluid into the sampling conduit 306. In certain embodiments, where the pumping device 318 is pumping a specific volume (for example, equivalent to the volume in the recovery conduit 307). The flow of the purging fluid in the sample conduit between the pumping device 318 and the second port 320 is directed to the recovery conduit 307 as represented by arrows 347.

Figure 7:
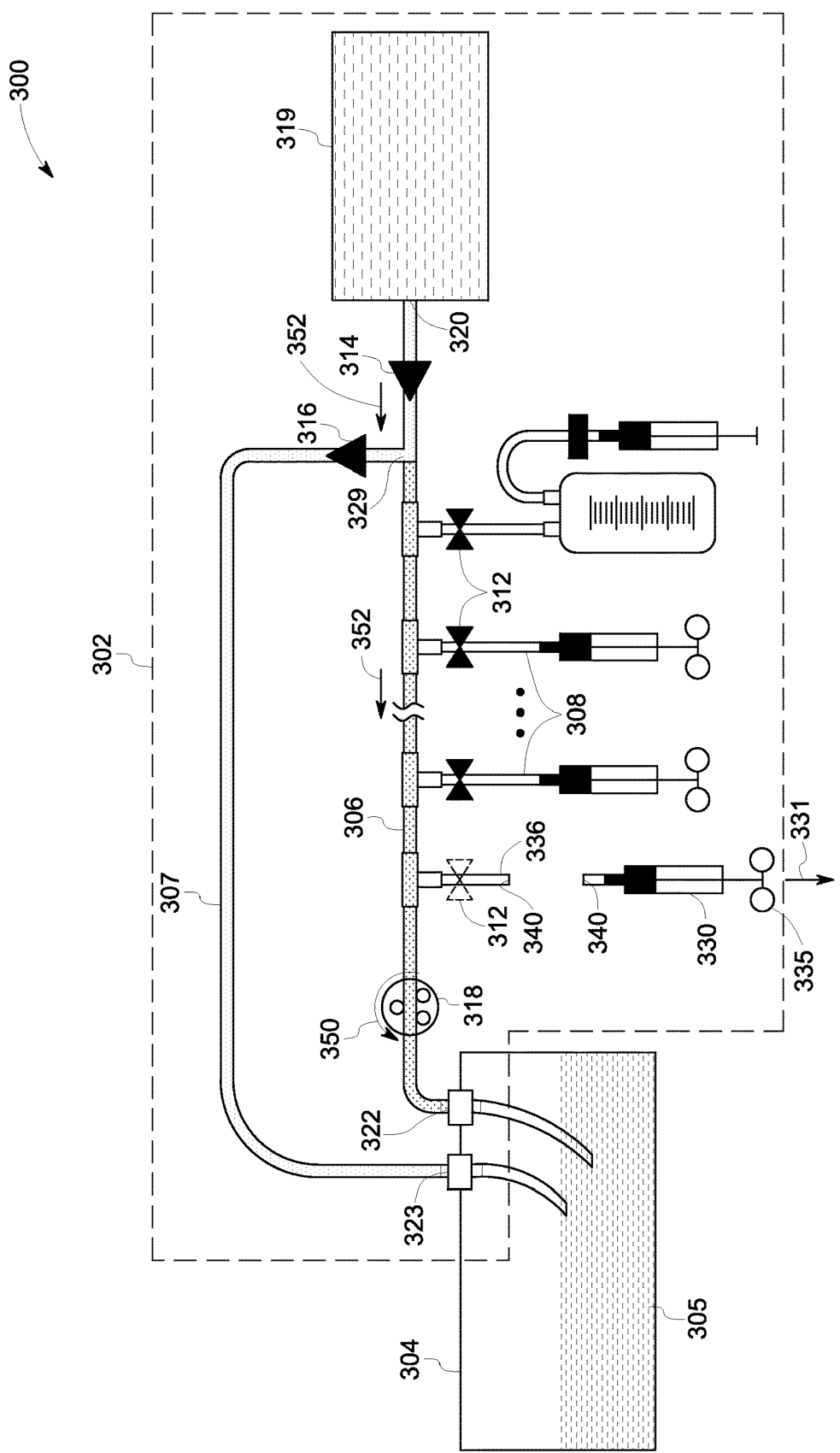

Subsequently, as illustrated in FIG. 7, the direction of rotation of the pumping device 318 may be once again reversed, as illustrated by arrow 350 to draw fresh purging fluid from the purging fluid source 319 into the sampling conduit 306, thereby purging any biological inoculum previously drawn into the sampling conduit when the purging fluid was used to purge the recovery conduit of residual sample. The pumping of the purging fluid is represented by arrow 352. The pumping of the purging fluid may be repeated one or more number to times based on an amount of purging fluid that is desirable to be introduced into the sample source 304.

Advantageously, the assemblies, systems and methods of the present specification enable effective withdrawal of a sample from a sterile sample source in an aseptic, rapid and cost-effective manner. Further, since the sampling assembly is pre-assembled and sterilized, the sampling assembly and the sampling process of the present specification permits a plurality of sampling instances whereby the sterile environment is safeguarded. In addition, since the series of steps to obtain a sample can be the same for each sampling instance, the pumping device can be pre-programmed to pump the correct volumes in the correct direction at each sub-step corresponding to the sampling instance.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A semi-automated sampling assembly configured for aseptic sampling at one or more instances from a sample source having a biological inoculum, the semi-automated sampling assembly comprising:
   a sampling conduit comprising a first port and a second port, wherein the first port of the sampling conduit is configured to be coupled to the sample source, wherein the second port of the sampling conduit is configured to be coupled to a purging fluid source;
   a recovery conduit comprising a first port and a second port, wherein the first port of the recovery conduit is configured to be coupled to the sample source, wherein the second port of the recovery conduit is coupled to the sampling conduit at a junction;
   a sampling loop comprising a portion of a tubing of the semi-automated sampling assembly disposed between the first port of the sampling conduit, the junction, and the first port of the recovery conduit, and wherein the biological inoculum is circulated in the sampling loop and returned to the sample source via the recovery conduit prior to a sampling instance;
   one or more sampling kits coupled to the sampling conduit; and
   a motorized pump coupled to the sampling conduit, wherein the motorized pump is configured to draw the purging fluid source, or a sample, or both, in the sampling conduit.

2. The semi-automated sampling assembly of claim 1, wherein the purging fluid source comprises a growth media source.

3. The semi-automated sampling assembly of claim 1, comprising two or more motorized pumps.

4. The semi-automated sampling assembly of claim 1, wherein the sampling conduit is configured to be in fluidic communication with the biological inoculum in the sample source.

5. The semi-automated sampling assembly of claim 1, further comprising a plurality of sampling kits operatively coupled to the sampling conduit.

6. The semi-automated sampling assembly of claim 5, wherein the plurality of sampling kits is coupled to the sampling conduit via corresponding sub-conduits of a plurality of sub-conduits, and wherein the corresponding sub-conduits are coupled to the sampling conduit.

7. The semi-automated sampling assembly of claim 6, wherein one or more sampling kits of the plurality of sampling kits comprise a sampling pillow, a sampling syringe, a sampling container, or combinations thereof.

8. The semi-automated sampling assembly of claim 6, further comprising a plurality of first flow controllers operatively coupled to one or more sub-conduits of the plurality of sub-conduits.

9. The semi-automated sampling assembly of claim 1, wherein the sampling conduit is a continuous conduit.

10. The semi-automated sampling assembly of claim 1, further comprising a plurality of flow regulators operatively coupled to at least a portion of the sampling conduit, at least a portion of the recovery conduit, or both.

11. The semi-automated sampling system of claim 1, further comprising a first flow regulator operatively coupled to the sampling conduit and disposed between the junction and the purging fluid source.

12. The semi-automated sampling assembly of claim 1, wherein the first port of the sampling conduit is configured to be fluidically coupled to the sample source.

13. The semi-automated sampling assembly of claim 1, wherein the first port of the recovery conduit is configured to be fluidically coupled to the sample source.

14. A semi-automated sampling system for sampling a biological inoculum at one or more instances in time, comprising:
    a sample source configured to house the biological inoculum;
    a semi-automated sampling assembly configured for aseptic sampling from the sample source having the biological inoculum, the semi-automated sampling assembly comprising:
        a sampling conduit comprising a first port and a second port, wherein the first port of the sampling conduit is configured to be coupled to the sample source, wherein the second port of the sampling conduit is configured to be coupled to a purging fluid source;
        a recovery conduit comprising a first port and a second port, wherein the first port of the recovery conduit is configured to be coupled to the sample source, wherein the second port of the recovery conduit is coupled to the sampling conduit at a junction;
        a sampling loop comprising a portion of a tubing of the semi-automated sampling assembly disposed between the first port of the sampling conduit, the junction, and the first port of the recovery conduit, and wherein the biological inoculum is circulated in the sampling loop and returned to the sample source via the recovery conduit prior to a sampling instance;
        one or more sampling kits connected to the sampling conduit; and
        a motorized pump coupled to the sampling conduit, wherein the motorized pump is configured to draw the purging fluid source, or a sample, or both, in the sampling conduit.

15. The semi-automated sampling system of claim 14, further comprising two or more motorized pumps.

16. The semi-automated sampling system of claim 14, wherein the purging fluid source comprises a growth media source.

17. The semi-automated sampling system of claim 14, wherein the junction is disposed between the purging fluid source and the one or more sampling kits.

18. The semi-automated sampling system of claim 14, further comprising a second flow regulator operatively coupled to the recovery conduit.

19. The semi-automated sampling system of claim 14, wherein a hold-up volume of the sampling conduit is greater than a hold-up volume of the recovery conduit.

\* \* \* \* \*